United States Patent
Steck

(10) Patent No.: US 6,620,133 B1
(45) Date of Patent: Sep. 16, 2003

(54) DELIVERY DEVICE WITH A SENSING UNIT

(75) Inventor: Jürg Steck, Kirchberg (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 09/508,942

(22) PCT Filed: Sep. 16, 1998

(86) PCT No.: PCT/CH98/00397

§ 371 (c)(1),
(2), (4) Date: Jun. 14, 2000

(87) PCT Pub. No.: WO99/15214

PCT Pub. Date: Apr. 1, 1999

(30) Foreign Application Priority Data

Sep. 25, 1997 (CH) ................................................ 2258/97

(51) Int. Cl.⁷ ............................ A61M 5/20; A61M 5/145
(52) U.S. Cl. ............................ 604/131; 604/30; 604/31; 604/65; 604/67; 604/187
(58) Field of Search ................................ 604/27, 30, 31, 604/65, 67, 118, 123, 124, 131, 151, 152, 154, 181, 186, 187, 207, 208, 218, 246

(56) References Cited

U.S. PATENT DOCUMENTS

| 3,884,228 | A |   | 5/1975 | Hahn |
|---|---|---|---|---|
| 4,457,751 | A | * | 7/1984 | Rodler ........................ 604/67 |
| 4,624,658 | A |   | 11/1986 | Mardorf |
| 4,950,246 | A |   | 8/1990 | Muller |
| 5,088,990 | A | * | 2/1992 | Hivale et al. ................. 604/67 |
| 5,593,390 | A |   | 1/1997 | Castellano |
| 5,728,074 | A |   | 3/1998 | Castellano |

FOREIGN PATENT DOCUMENTS

| DE |   | 3840000 | 11/1988 |
|---|---|---|---|
| EP |   | 0143895 | 4/1986 |
| GB |   | 2115495 | 9/1983 |
| WO | WO | 9316740 | 9/1993 |
| WO | WO | 9627398 | 2/1996 |
| WO | WO | 9730742 | 8/1997 |

* cited by examiner

*Primary Examiner*—J. Casimer Jacyna
(74) *Attorney, Agent, or Firm*—Dorsey & Whitney LLP

(57) ABSTRACT

An injection device includes a timing device that is triggered by an injection. After a predetermined period of time, the timing device triggers a sensing device that produces a signal, such as an audible tone. The signal alerts the user that a sufficient amount of time has passed and the injection device can be removed.

29 Claims, 2 Drawing Sheets

DELIVERY DEVICE WITH A SENSING UNIT

This application claims the priority of PCT application PCT/CH98/00397, filed Sep. 16, 1998, and of Swiss application 2258/97, filed Sep. 25, 1997, both of which are incorporated herein by reference.

BACKGROUND

The invention relates to a device for delivering an injectable product including an acoustic or vibrational sensing unit as set forth in the preamble of claim 1.

Devices like those of the invention preferably concern delivery devices for injecting or infusing a liquid solution of an active substance, preferably a liquid medicament. In particular it is preferred that such devices relate to portable devices, especially in the form of so-called injection pens always referred to in the following representative for others.

Injection pens as known, for example, from WO 93/16740, but also pumping devices, as known for example from EP-B-0 143 895, for infusing or injecting/infusing solutions of active substances comprise a housing in which a container, containing the product, can be accommodated in an accommodation provided for this purpose. Shiftingly mounted in the container is a piston. When the piston is urged in the delivery direction a dose of the product is dispensed, due to it being displaced by the piston. For this purpose, the container, generally an ampule, is fixed in the accommodation such that a driven member of a delivery mechanism urges the piston in forward direction to deliver the product. The delivery mechanism comprises substantially two elements, the aforementioned driven member and a drive means. The driven member protrudes into the container—in the direction of the piston—when the container is accommodated in the housing. The drive means engages the driven member in such a way that actuation of the drive means urges the driven member in the delivery direction. In known injection pens having spindle drives the drive means is actuated both by rotation, namely for the purpose of dispensing,the product dose to be delivered by the next injection, and also by a linear shift in the delivery direction of the piston, namely by a manually exerted pressure. However, also conceivable is a delivery mechanism whose driven member comprises a saw tooth structure and the drive means is equipped with the corresponding mating elements. In known pumping devices, having spindle drives and operated by electric motors, the drive means is actuated only by rotation. This rotation prompts, in turn, an advancement of the driven member in forward direction which, however, in pumping devices is generally translated directly to the piston.

The liquid solution of the active substance is discharged through a cannula mounted on the injection pen. The rear end of the cannula flowingly communicates with the active substance solution while the front end protrudes from the injection pen and can pierce the skin. In pumping devices, the cannula is located at the end of an infusion tube opposite the pump.

For administering the active substance solution the cannula is first pushed into the skin and, subsequently, the active substance solution is dispensed via the cannula into the body either by manual or motor driven actuation of the delivery mechanism. Dispensing occurs such that, upon actuation of the delivery mechanism, the piston is shifted by a certain travel in the direction of the ampule orifice, as a result of which first a relatively large amount of active substance is dispensed and, subsequently, during a relatively short time interval, the active substance is delivered only in droplets droplets through the cannula. However, where highly concentrated solutions of active substance are concerned, this last dribble is not to be ignored. This is why the patient is requested, after having actuated the delivery mechanism, to leave the cannula in place hypodermically for 5 to 10 seconds so that these last droplets likewise enter the body. It is often the case, however, that the patient lacks the necessary timing and removes the cannula prematurely.

Known from WO 97/30742 is an apparatus which solves the above problem by incorporating an electronic display. However, this fails to be convincing since users, in particular users of insulin delivery devices, often suffer from impaired vision and thus visual displays are rather unfortunate. In addition to this, visual displays in apparatuses in use are a nuisance since they always require that the patient, while using the apparatus, has a good view of the display.

SUMMARY

This is where the invention provides a solution. The invention is based on the object of creating a device for delivering a product dose which alerts the patient to remove the cannula from the skin by emitting an acoustic signal or by means of vibration.

The invention achieves the above object with a device comprising the features as set forth in claim 1.

The advantages attained by the invention are substantially to be appreciated in that the acoustic signal or vibration alerts the patient in a simple manner to the fact that the last droplets of an injection/infusion have entered the body and that, thus, the cannula can be removed from the body.

Preferred example embodiments of the invention will now be detailed with reference to the drawings in which:

DETAILED DESCRIPTION

Figure 1:
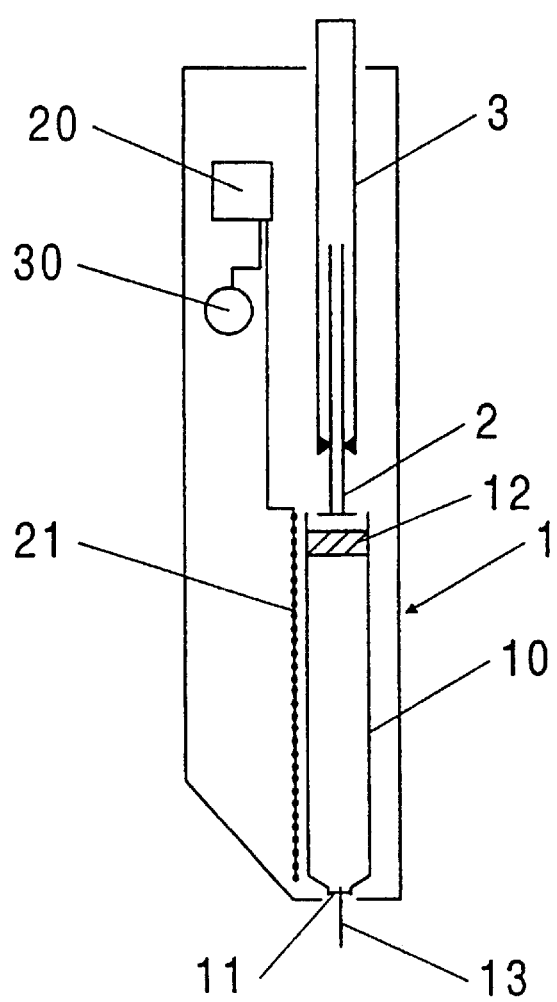
FIG. 1 illustrates a delivery device with a sensing unit in accordance with the invention

Referring now to FIG. 1, there is illustrated the delivery device in accordance with the invention comprising a housing 1 in which an ampule 10 is mounted. Accommodated in the ampule, between a front orifice 11, mostly configured as a septum, and a sliding piston 12, is a solution of an active substance.

The delivery mechanism comprises a driven member 2 and a drive means 3 engaging the latter. By actuation of the drive means 3 the driven member 2 is shifted in forward direction. Setting the product dose to be administered is done by increasing the total travel of drive means 3 and driven member 2. It is by this selective increase in the total travel of drive means 3 and driven member 2 that the piston 12 of the ampule 10 is shifted in the direction of the ampule orifice 11, resulting in the product being dispensed due to a displacement through a cannula 13 mounted on the ampule orifice 11.

Within the housing 1 is a device 30 devised to output, after a timed delay, an acoustic or vibrational signal when the piston 12 has covered the total travel desired and, thus, corresponding delivery of the product dose has occurred. For solving this problem there are various solutions. Thus, by means of sensors 21, arranged along the ampule, it can be respectively sensed when the piston 12 has come to a standstill after a specific delivery movement (FIG. 1). When this standstill is sensed, a time lapse system 20—preferably a mechanical or an electronic control—is activated, upon lapse of which a signal is output by the acoustic or vibrational sensing unit 30 to inform the patient that a specific time unit has elapsed since termination of the shift of the piston 12 in the direction of the ampule orifice 11. A time delay of 5 to 10 seconds between the last movement of the plunger and the acoustic or vibrational signal is deemed as ideal.

Figure 2:
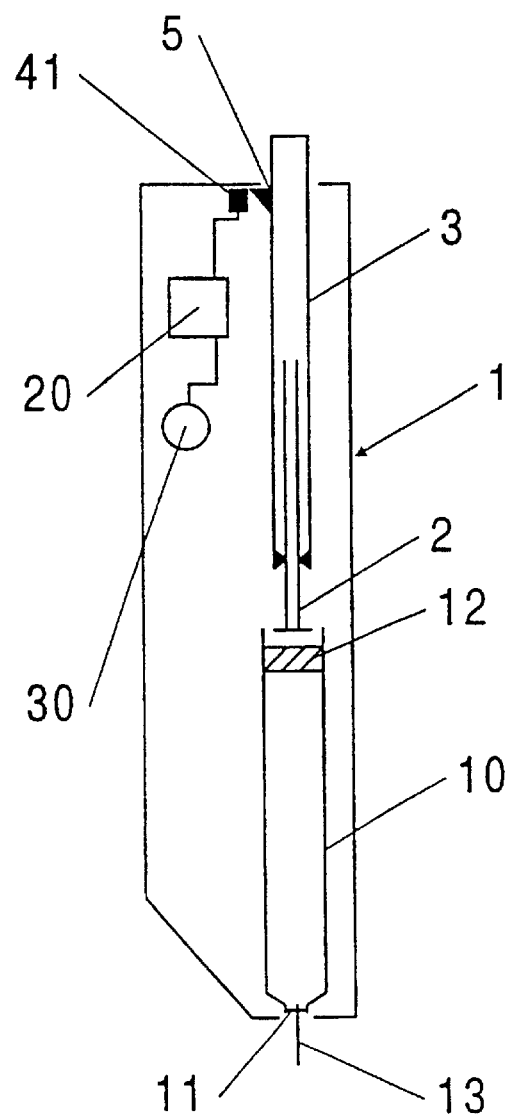
FIGS. 2–4 illustrate alternate example embodiments of the sensing unit and delivery device
Figure 3:
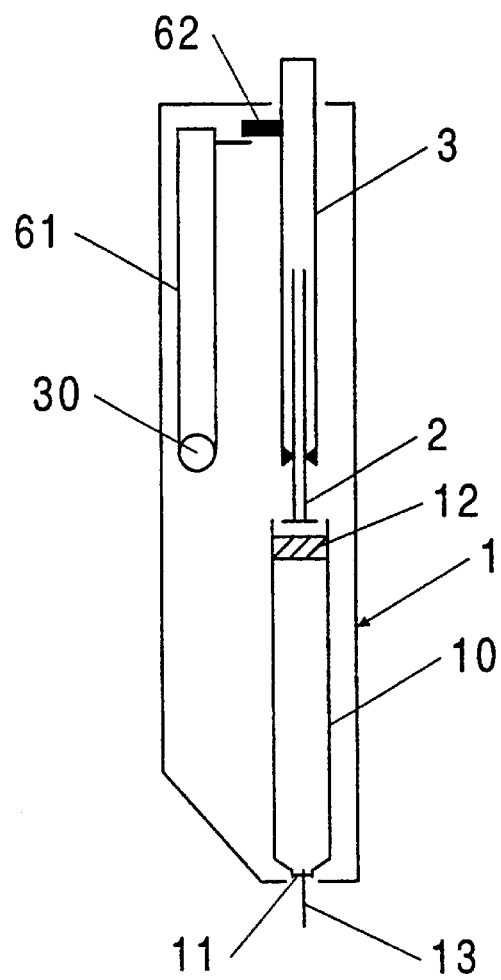

In manually activated delivery devices, latching means 5 may be arranged on the drive means 3 which latch in place in the housing 1 after activation (FIG. 2). This latching action activates means 41 which output a pulse to the time lapse system 20 and, upon lapse thereof, a signal is output by the acoustic or vibrational sensing unit 30. The aforementioned means 41 may be sensors, which sense the latching action, or a switch, activated by the latching means. Likewise conceivable is the use of a wind-up timer 61, whereby actuation of the drive means 3 simultaneously winds up the timer 61 via a connecting element 62 (FIG. 3). In this arrangement, the sensing unit 30 is part of the wind-up timer 61.

Figure 4:
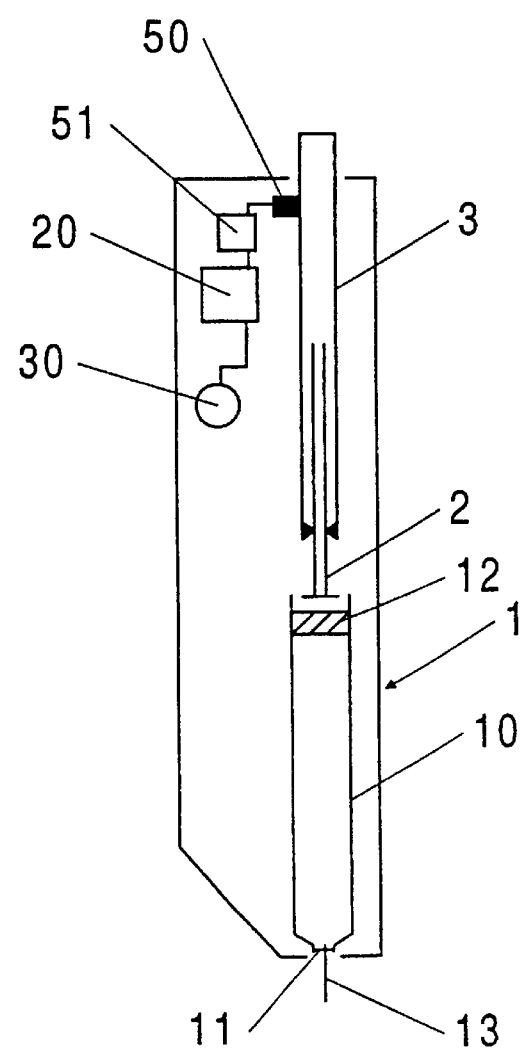

As illustrated in FIG. 4, in motor driven delivery devices, a motor control 51 can also output, in addition to the stop command to the motor 50, a pulse to the time lapse system 20, upon lapse of which, a signal is output by the acoustic or vibrational sensing unit 30.

The sensing unit may also be arranged outside of the delivery device and be activated by means of an electrical or radio connection.

What is claimed is:

1. A device for injecting or infusing a liquid product from a container, said device comprising a delivery mechanism, a time delay element and a sensing unit, wherein the time delay element activates the sensing unit, wherein said container is an ampule, equipped with a piston, in which the liquid product is contained between said piston and an ampule orifice.

2. The device according to claim 1, wherein the delivery mechanism is manually operated.

3. The device according to claim 1, wherein the delivery device is motor driven.

4. The device according to claim 1, wherein said activation occurs just before or upon termination of actuation of the delivery mechanism.

5. The device as set forth in claim 1, wherein the time delay elements are mechanical elements.

6. The device as set forth in claim 1, wherein said time delay elements are electrical elements.

7. The device as set forth in claim 1, wherein said time delay elements are connected to a time lapse system.

8. The device as set forth in claim 7, wherein said time lapse system is one of a mechanical or an electronic control.

9. The device as set forth in claim 1, said delivery mechanism comprising latching means for coupling with a mating element upon termination of the actuation of said delivery mechanism.

10. The device as set forth in claim 9, wherein said latching means acts on a switch to activate a time lapse system for measuring a period of time at the end of which said sensing unit is activated.

11. The device as set forth in claim 1, wherein said time delay element senses the termination of the actuation of said delivery mechanism, as a result of which a time lapse system is activated for a period of time, and upon the lapse of said period of time, said sensing unit is activated to send a signal.

12. The device as set forth in claim 1, wherein, upon actuation of said delivery mechanism a mechanical delay switch is activated.

13. The device as set forth in claim 12, wherein said mechanical delay switch is a wind-up timer.

14. The device as set forth in claim 1, wherein said delivery mechanism comprises a motor with a controller, said controller activating a time lapse system before, after or simultaneously with a stop command for said motor, and activating said sensing unit upon lapse of said time lapse system.

15. The device as set forth in claim 1, wherein said delivery mechanism comprises a rod-shaped driven member and a drive means, said driven member having a structured outer shell and said drive means having a matching inner shell arranged at least partly around said driven member.

16. The device as set forth in claim 1, wherein said delivery mechanism comprises a rod-shaped driven member and a drive means, said driven member having a structured inner shell and said drive means having a matching outer shell arranged at least partly within said driven member.

17. The device as set forth in claim 1, wherein the sensing unit senses termination of said movement of said piston, upon which said time delay element is activated and then, upon lapse of the time delay element, said sensing unit is activated to send a signal.

18. The device as set forth in claim 17, wherein said sensing unit is within said device.

19. The device as set forth in claim 17, wherein said sensing unit is outside said device.

20. A device for injecting or infusing a liquid product from a container, said device comprising a handheld housing including a delivery mechanism, a time delay element and a sensing unit, wherein the time delay element activates the sensing unit and, wherein said container is an ampule, equipped with a piston, in which the liquid product is contained between said piston and an ampule orifice.

21. The device as set forth in claim 20, wherein said delivery mechanism comprises a rod-shaped driven member and a drive means, said driven member having a structured outer shell and said drive means having a matching inner shell arranged at least partly around said driven member.

22. The device as set forth in claim 20, wherein said delivery mechanism comprises a rod-shaped driven member and a drive means, said driven member having a structured inner shell and said drive means having a matching outer shell arranged at least partly within said driven member.

23. The device as set forth in claim 20, wherein the sensing unit senses termination of said movement of said piston, upon which said time delay element is activated and then, upon lapse of the time delay element, said sensing unit is activated to send a signal.

24. The device as set forth in claim 23, wherein said sensing unit is within said device.

25. The device as set forth in claim 23, wherein said sensing unit is outside said device.

26. A device for infecting or infusing a liquid product from a container, said device comprising an injection pen including a delivery mechanism, a time delay element and a sensing unit, wherein the time delay element activates the sensing unit and, wherein said container is an ampule, equipped with a piston, in which the liquid product is contained between said piston and an ampule orifice.

27. The device as set forth in claim 26, wherein said delivery mechanism comprises a rod-shaped driven member and a drive means, said driven member having a structured outer shell and said drive means having a matching inner shell arranged at least partly around said driven member.

28. The device as set forth in claim 26, wherein said delivery mechanism comprises a rod-shaped driven member and a drive means, said driven member having a structured inner shell and said drive means having a matching outer shell arranged at least partly within said driven member.

29. The device as set forth in claim 26, wherein the sensing unit senses termination of said movement of said piston, upon which said time delay element is activated and then, upon lapse of the time delay element, said sensing unit is activated to send a signal.

\* \* \* \* \*

UNITED STATES PATENT AND TRADEMARK OFFICE
CERTIFICATE OF CORRECTION

PATENT NO.    : 6,620,133 B1
DATED         : September 16, 2003
INVENTOR(S)   : Jürg Steck It is certified that error appears in the above-identified patent and that said Letters Patent is hereby corrected as shown below:

Column 4,
Line 56, please delete "infecting" and insert -- insecting --.

Signed and Sealed this

Fifth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,620,133 B1
DATED : September 16, 2003
INVENTOR(S) : Jürg Steck

It is certified that error appears in the above-identified patent and that said Letters Patent is hereby corrected as shown below:

<u>Column 4,</u>
Line 56, delete "infecting" and insert -- injecting --.

Signed and Sealed this

Thirteenth Day of June, 2006

JON W. DUDAS
*Director of the United States Patent and Trademark Office*